(12) United States Patent
Wadhawan et al.

(10) Patent No.: US 8,600,471 B2
(45) Date of Patent: Dec. 3, 2013

(54) CATHETER WITH A SENSING REGION FOR REDOX REACTIONS

(75) Inventors: Jay Wadhawan, Beverley (GB); John Greenman, Cottingham (GB); Magdi El-Habbal, North Ferriby (GB); Linda Shields, Townsville (AU); Cameron Imrie, Derry (GB); Barbara Elliott, Walkington (GB)

(73) Assignee: The University of Hull, Hull (GB)

(*) Notice: Subject to any disclaimer, the term of this patent is extended or adjusted under 35 U.S.C. 154(b) by 989 days.

(21) Appl. No.: 12/303,427

(22) PCT Filed: Jun. 8, 2007

(86) PCT No.: PCT/GB2007/050326
§ 371 (c)(1),
(2), (4) Date: Dec. 4, 2008

(87) PCT Pub. No.: WO2007/141579
PCT Pub. Date: Dec. 13, 2007

(65) Prior Publication Data
US 2010/0016699 A1    Jan. 21, 2010

(30) Foreign Application Priority Data
Jun. 8, 2006 (GB) .................................. 0611297.3

(51) Int. Cl.
*A61L 29/16* (2006.01)
*A61B 5/05* (2006.01)

(52) U.S. Cl.
USPC ........................................................ 600/361

(58) Field of Classification Search
None
See application file for complete search history.

(56) References Cited

U.S. PATENT DOCUMENTS

| 4,381,011 | A | * | 4/1983 | Somers, 3rd | 600/350 |
| 4,632,119 | A | * | 12/1986 | Reichstein | 600/350 |
| 4,871,442 | A | * | 10/1989 | Yamaguchi et al. | 204/418 |

FOREIGN PATENT DOCUMENTS

| EP | 0245168 A2 | 11/1987 |
| EP | 1774985 A | 4/2007 |
| WO | 9217150 A | 10/1992 |
| WO | 2004054430 A2 | 7/2004 |
| WO | 2006003960 A | 9/2006 |
| WO | 2007064835 A | 6/2007 |

OTHER PUBLICATIONS

Saum et al., "Use of substrate coated electrodes and AC impedance spectroscopy for the detection of enzyme activity," Biosensors and Bioelectronics, 1998, vol. 13, Issue 5, pp. 511-518.*
Wain et al., "Electrochemical Studies of Vitamin K1 Microdroplets: Electrocatalytic Hydrogen Evolution," Chem. Phys. Chem., 2003, vol. 4, Issue 9, pp. 974-982.*
A printout http://en.wikipedia.org/wiki/Electrocatalyst, retrieved Jun. 5, 2012.*

(Continued)

*Primary Examiner* — Shafiqul Haq
*Assistant Examiner* — Galina Yakovleva
(74) *Attorney, Agent, or Firm* — Quarles & Brady LLP

(57) ABSTRACT

The present disclosure relates to catheters, for example a catheter which is adapted such that the user is able to determine whether it has been correctly positioned within 5 the subject. Also included in the present disclosure are means for detecting the position of the catheter and combinations of a catheter and processors for determining the positioning of the catheter. The present disclosure also relates to methods of determining the position of a catheter in, for example, a human or animal body.

19 Claims, 6 Drawing Sheets

(56) References Cited

OTHER PUBLICATIONS

Metheny N. et al: Detection of Inadvertent Respiratory Placement of Small-Bore Feeding Tubes a Report of 10 Cases: Heart and Lung, vol. 19, No. 6. 1990, pp. 631-638, XP008083373, ISSN: 0147-9563.
Westhus Nina: "Methods to test feeding tube placement in children" MCN. The American Journal of Maternal Child Nursing Sep.-Oct. 2004, vol. 29, No. 5, Sep. 2004, pp. 282-287; qui, XP 008083377, ISSN: 0361-929X.
PCT International Search Report for PCT/GB2007/050326 of which the subject application is a national phase filing; mailed Apr. 10, 2007.
European Office action for corresponding application EP 07733747.5 citing two above-listed foreign references, mailed Dec. 20, 2011, 5 pages.

* cited by examiner

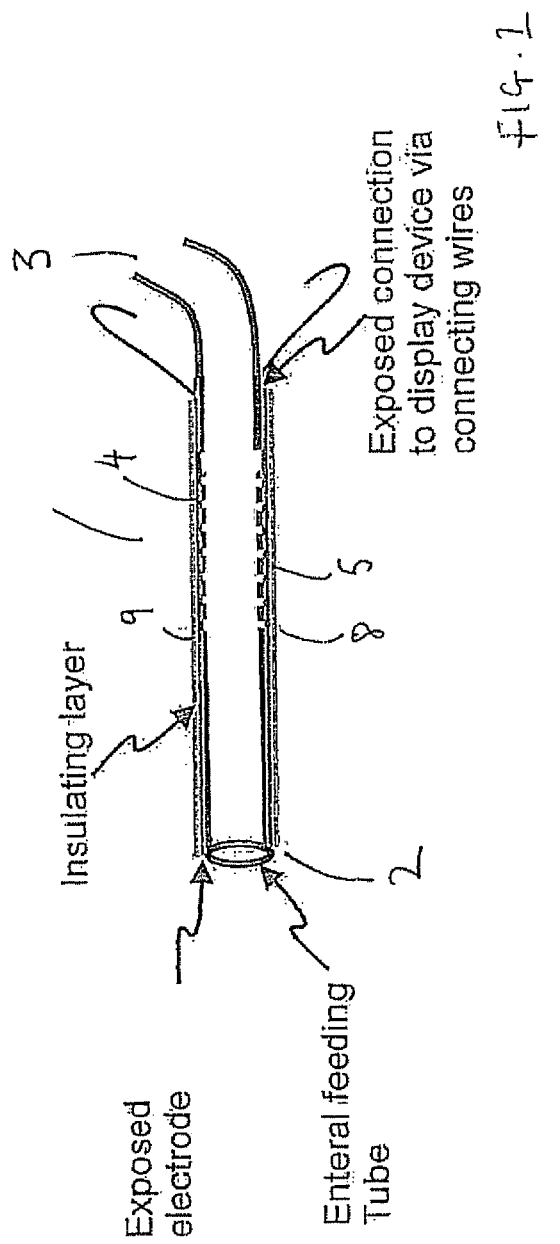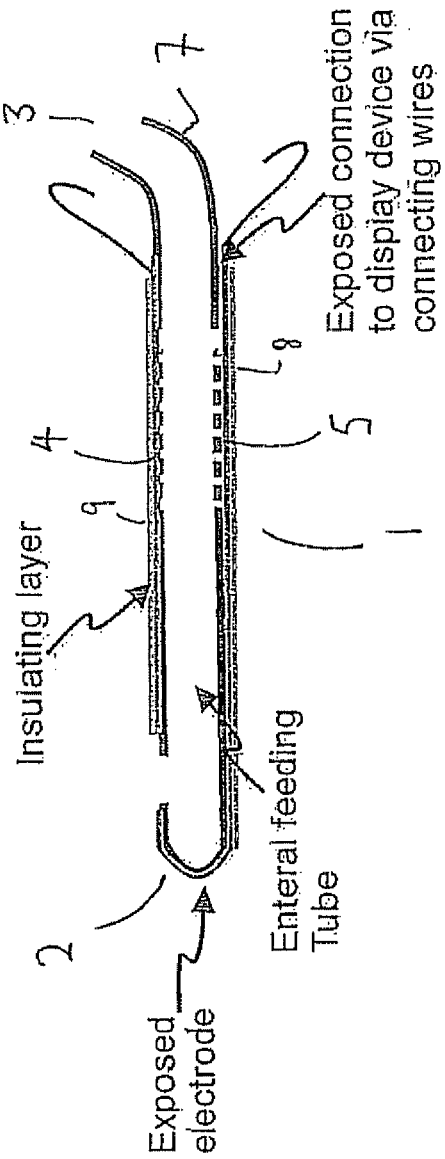

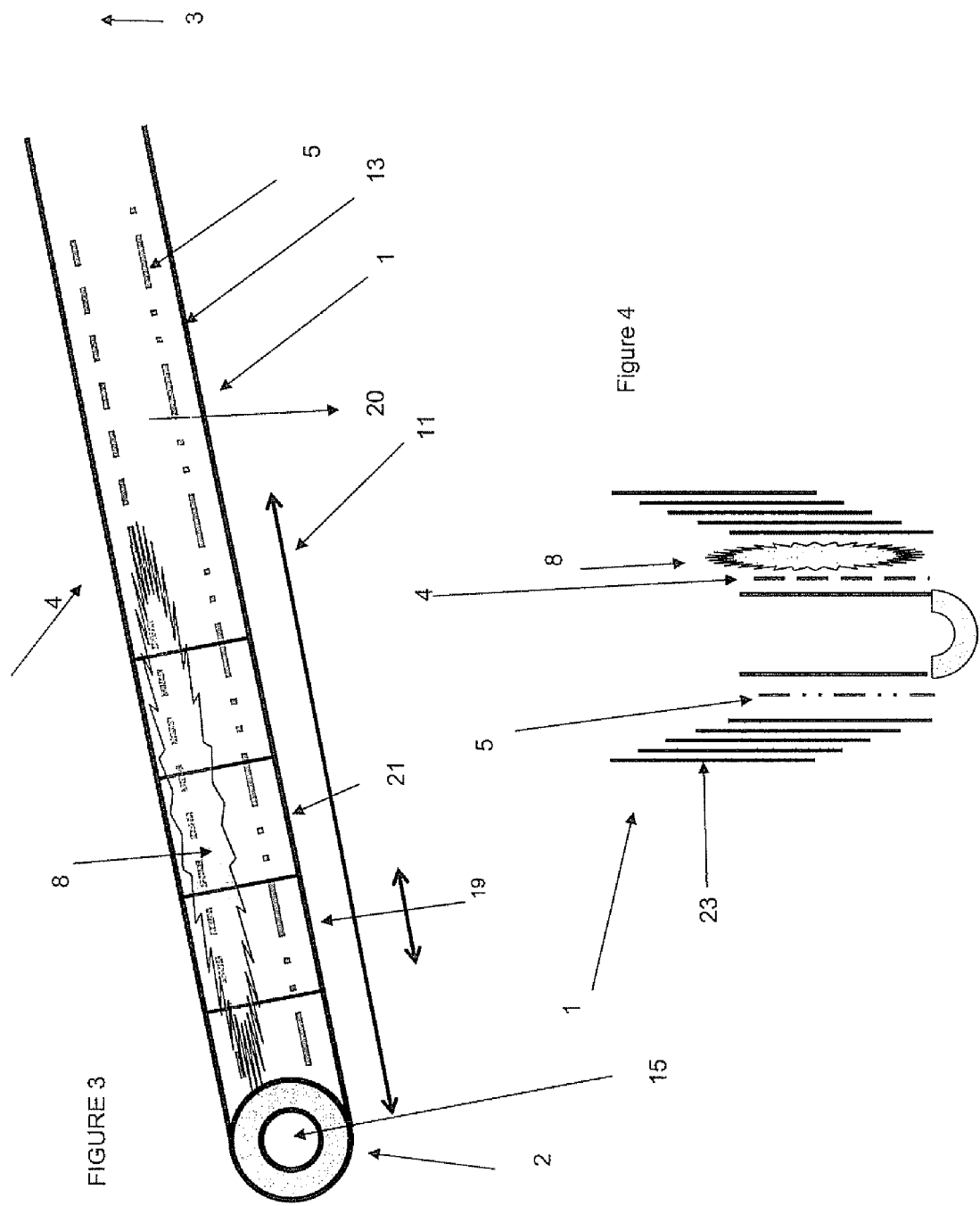

CATHETER WITH A SENSING REGION FOR REDOX REACTIONS

CROSS REFERENCE TO RELATED APPLICATIONS

This application represents the national stage application of International Application PCT/GB07/050326, filed 08 Jun. 2007, which claims the benefit of Great Britain Patent Application 0611297.3 filed 08 Jun. 2006, which are incorporated herein by reference in their entirety for all purposes.

FIELD OF THE INVENTION

The present disclosure relates to catheters, for example catheters which are adapted such that the user is able to determine whether it has been correctly positioned within the subject. Also included in the present disclosure are means for detecting the position of the catheter and combinations of a catheter and a detecting means. The present disclosure also relates to methods of determining the position of a catheter in, for example, a human or animal body, as well as other subject matter.

BACKGROUND TO THE INVENTION

Medical, nursing and veterinary care often involves procedures where instruments are introduced blindly into the human or animal body. X-ray and fibre-optic imaging may be used to guide certain high risk procedures, but the vast majority of routine procedures are conducted "blind" such that the practitioner cannot see where the instrument is going nor clearly identify its final location.

Catheters are tubes, which typically drain fluid from, or introduce fluid into, the body. Catheters have been available since the eighteenth century, and their use is now common practice in medicine. They are used extensively with babies in neonatal units and catheters may be inserted, for example, via the nose or mouth into the stomach or jejunum for feeding. Nasogastric or nasojejunal feeding is the preferred method for providing nutritional support to critically ill patients of all ages. Feeding catheters may also be inserted directly into the stomach through an incision in the abdominal wall (known as gastrostomy tubes).

There are two main categories of catheters which are currently used for providing nutritional support. One includes firm, large bore, plastic tubes which are typically used for short term feeding. The other category includes softer, narrow bore, polyurethane tubes, which show less side effects such as ulceration and bleeding of the nose, pharynx and stomach than the firm tubes, but which are not without risks themselves. In particular, as they require a stylet for insertion, tracheopulmonary injuries associated with insertion of these tubes have been reported (Rubenoff R and Ravich WJ, Pneumothorax due to nasogastric feeding tubes, *Archives of Internal Medicine* 149 184-188, (1989)).

Whichever type of catheter is being used, and regardless of the age of the patient, the key issue for the practitioner is verification of the correct placement of the catheter. This must be done when the catheter is initially passed and, for example, before every feed or administration of medication. Particular problems can arise with specific groups of patients such as neonates or critically ill patients who are paralysed and ventilated.

It is often necessary, particularly in pediatrics, to teach non-medical persons (e.g. parents) how to use catheters to administer enteral feeds and medication, so that they may deliver care either under supervision in hospital, or at home where there is no direct supervision or easy access to nursing support.

A feeding catheter may be considered to be misplaced if it is placed in the respiratory tract, oesophagus, or intestine if gastric feeding is desired, or in the stomach if intestinal feeding is the intention. Whilst serious complications and death are rarely reported, malpositioned catheters can cause problems for patients, such as intolerance of feeds. Having a catheter passed is unpleasant for both adults and children, and having to have this process repeated because the catheter is in the wrong place, or because the location cannot be verified, is costly in both time and distress to the patient. Those administering the tube, be they nurses, doctors or parents/carers, the fear of pouring feed into the lungs creates considerable anxiety and is not conducive to promoting confidence.

A variety of methods have been, or are currently, used to verify the position of feeding catheters. However, published research studies that have been conducted have found such clinical indicators to be unreliable. (Metheny et al., Nutrition in Clinical Practice, 19(5) 487-495 (2004); Rassias et al., Clinical Care 2 (1) 25-28 (1998); Rubenoff and Ravich, loc. cit.; Bohnker, Artman and Hoskins, Nutritional Clinical Practice. 2 203-209 (1987)). The most common methods for verifying catheter placement including the following:

Auscultation involves injecting air into the catheter and listening for a loud sibilance as this air enters the stomach. This procedure is not only unreliable, but may also be dangerous if the tube is misplaced. For example, if the tube is wrongly placed in the lungs and air is injected directly into the pulmonary parenchyma, it is possible to induce a pneumothorax (Rubenoff and Ravich, loc. cit.). In neonates, the stomach and lungs are so close together that it is virtually impossible to distinguish between the sound of air being injected into the stomach and air injected into the bronchi. Even in adult patients the sound of injected air can be heard over the epigastric region regardless of the location of the tube.

Observing patients for respiratory distress (such as coughing, choking, dysphagia or the inability to speak) is also an unreliable indicator of tube misplacement. Small bore tubes can enter the respiratory tract with few, if any, symptoms (Metheny et al Heart Lung Journal of Acute Critical Care 19, 631-638 (1990)) and large bore tubes can enter the respiratory tract with no symptoms particularly if the patient is unconscious (Rassias et al., loc. cit.). Observing for bubbling when the end of the tube is placed in water is unreliable as the stomach may also contain air and produce bubbling.

Testing aspirate of the tube, for pH for example, has been used for some years. Studies have reported that, excluding radiographic confirmation, a pH reading of 4 or less is the most reliable indicator of tube placement in the stomach (Metheny et al., loc. cit., Metheny and Titler, Am. Journal of Nursing 101 36-45, (2001)). However, whilst it is claimed that the pH testing of aspirate is a simple and easy test in the clinical setting (Westhus, Am. Journal Maternal Child Nursing 29 282-291, (2004)), there are problems with this method. Neonates in particular pose specific considerations as they have an intrinsically higher gastric pH. Medications and continuous feeding may also affect the gastric pH, and intestinal and pulmonary aspirate has a pH greater than 5 so this method could not be used to differentiate between these two locations. The pH of aspirate is also unable to act as a means to differentiate between oesophageal and gastric placement as oesophageal reflux can result in both acidic and alkaline readings.

Laboratory tests for gastrointestinal enzymes, pepsin and trypsin are more accurate predictors of placement (Gharpure et al., Critical Care Medicine 25 2962-2966, (2000)) but at present there are no simple bedside tests for these enzymes. In addition, like determination of pH value, such tests would require the aspiration of fluid from the stomach.

Very few of the research studies on assessment of aspirate address the difficulty that can occur when trying to obtain aspirate from patients. This is particularly a problem in neonates and when using fine bore tubes. The National Patient Safety Agency offers advice on how to address the problems of obtaining aspirate from neonates which nurses should follow. However, anecdotal evidence suggests that nurses may use syringes of an inappropriate size to obtain aspirate which may damage the gastric mucosa of the baby or cause the catheter to collapse, both of which are potentially harmful and at least require the tubes to be removed and a new one to be inserted. Tubes with built in pH probes that do not rely on obtaining aspirate have been developed and used clinically. However, they have been mainly used to distinguish between placement in the stomach and small intestine rather than between gastric and pulmonary placement (Berry, Shoettker and Orr, Nutrition 10 419-423 (1994)). Such tubes are expensive and require special training to be used.

X-ray examination has long been considered the only definitive determination of the placement of catheters. Thus, catheters generally are either radiopaque or have a radiopaque strip so that they may be seen via X-ray examination. However, interpretation of X-rays, particularly in the critically ill can be difficult and errors in interpretation can occur resulting in significant morbidity (Rassias et al., loc. cit.). Exposure to radiation also carries significant long term risks, particularly in neonates.

Thus, there is no current, definitive, non-radiographic method to determine correct placement of a catheter, for example by differentiating between respiratory, oesophageal, gastric and small bowel placement.

The present invention therefore aims to overcome, or ameliorate, these problems in the prior art, and provide products and methods for determining correct placement of a catheter within a bodily passage or cavity.

BRIEF SUMMARY OF THE DISCLOSURE

In one aspect of the present invention, there is provided a catheter having an external end which, in use, remains outside the subject being catheterised (distal end) and an insertion end (proximal end) for introduction into a pre-selected location in a subject, and a pair of electrical conductors extending therebetween which in use have a constant potential difference between them, wherein at least one of said electrical conductors is in electrical contact with a binding partner for a biological agent specific to said pre-selected location, such that in use binding of a biological agent to said binding partner changes a current flowing in said electrical conductors.

In one, non-limiting embodiment, the binding partner may be a redox reagent or an intermediary in a redox reagent, e.g. a reduced form of the redox reagent or an oxidised form of the redox reagent. In an embodiment, the biological agent may be for example protons located within the pre-selected location.

In an aspect of the present invention, there is provided a catheter comprising a first end portion having a sensing region comprising at least one redox reagent which is in electrical connection with an electrode. In one embodiment, the redox reagent undergoes a redox reaction when the sensing region is in a body of a subject at a rate dependent on the environment of the sensing region. The rate may be nil or substantially nil in one or more environments. In one class of embodiments the redox reagent undergoes a measurable redox reaction in the pre-selected location.

The present invention provides a catheter which is suitable for insertion into a subject's body. The provision of a catheter which comprises a binding partner, e.g. a redox reagent, in electrical communication with an electrode (also referred to herein as an electrical conductor) can result in an environment-specific or environment-dependent electrical signal being produced when the catheter is inserted into a subject's body. The electrical signal may then be processed e.g. by an information processor e.g. a transducer as described herein and used to determine whether the catheter has been inserted into the desired bodily environment; such catheters form one embodiment of the invention. The electrical signal produced when the catheter is inserted can then be compared with a standard (a predetermined level of electrical signal), to determine whether the catheter is correctly located; thus, the standard may represent a threshold on one side of which current level indicates correct insertion and on the other side of which current indicates that the catheter is, or may be, incorrectly inserted. Thus, if the catheter has been inserted into an incorrect environment, the redox reagent undergoes a redox reaction at a rate indicative of incorrect insertion (too high or too low). In an embodiment, when the catheter (more precisely, its sensing region) is located in an incorrect environment, the reagent either does not undergo a redox reaction, or undergoes a redox reaction at a lower level than would be predicted if it were inserted into the correct environment (the pre-selected locater). In this embodiment, the electrical signal produced when the catheter is incorrectly located will be lower than the pre-determined level, indicating the incorrectness of the catheter positioning, thus allowing for the repositioning of the catheter.

An apparatus which can be simple to use and which offers a definitive answer to the question of whether a catheter has been placed in a correct environment in a subject's body is therefore provided by the present invention.

In an aspect of the present invention, there is provided a catheter for insertion into a subject's body, which comprises at a proximal end thereof a sensing region for insertion into the subject's body, wherein the sensing region comprises a redox reagent.

In one aspect of the present invention, there is provided a sensor for inserting into a subject's body comprising a redox reagent which is capable of undergoing a redox reaction in a pre-selected bodily environment to form a redox product and an agent which is capable of causing or facilitating regeneration of the redox reagent from the redox product. In one embodiment, the sensor comprises a combination of redox reagent and regenerating agent which permits a continuous redox reaction to take place when the sensor is inserted in a pre-selected location. In an embodiment, the sensor comprises a pair of electrodes to which the potential difference is applied by an external d.c. power source during use to initiate a primary redox process.

In an aspect of the present invention, there is provided a catheter comprising a pair of electrodes which are applied to the outer surface of the tubular member. Also provided is a catheter comprising a tubular member and a pair of electrodes formed on, or coated on, the outer surface of the tubular member. In one embodiment, the pair of electrodes are formed from metallic paint. In one embodiment, the catheter comprises a tubular member to which the electrodes are applied.

The invention also relates in one aspect to a combination of a catheter as defined herein and an information processor for detecting or measuring an electrical signal. The electrical signal may be generated by binding of the binding partner to a biological agent. In one embodiment, the electrical signal may be generated by a redox reaction involving the redox reagent. In one embodiment, the sensor or catheter comprises at least two electrodes. In one embodiment, the combination may further comprise means for applying a potential difference between the electrodes.

In a further aspect of the present invention, there is provided a method of detecting the location of a catheter, comprising detecting or measuring an electrical property of a catheter having an insertion end in a subject and an external end outside the subject, the catheter further having a pair of electrical conductors extending between said ends and, in electrical contact with at least one of the electrical conductors, a binding partner for a biological agent specific to said pre-selected location, the electrical conductors having a constant potential difference applied across them. In one embodiment, the electrical property is the current passing through the electrical conductors.

As used herein, the term "proximal end" of the catheter refers to an end of the catheter which is inserted into the subject. Thus, the proximal end is the end of the catheter which is situated in the pre-selected bodily environment during use. In one embodiment, the sensing region of the catheter is located at or proximate to the proximal end of the catheter.

As used herein, the term "distal end" of the catheter refers to an end of the catheter which is at the opposite end of the catheter to the proximal end. The distal end of the catheter is typically situated outside the subject's body during use and can be the end of the catheter which is located closest to an operator of the catheter. In one embodiment, the distal end of the catheter is connectable to an information processor e.g. a signal transducer which is located external to the subject's body.

Methods are also provided herein, which are suitable for both medically trained and non-medically trained personnel to use to determine whether a catheter or sensor has been inserted into the correct environment in a subject's body. Typically, such methods involve use of the catheters as described herein.

In one aspect of the present invention, there is provided a method for placing a catheter inside a gastrointestinal tract comprising:
(a) inserting a proximal end of a catheter, which comprises a sensing region as defined herein into a body cavity or passage;
(b) detecting or measuring an electrical signal produced as a result of insertion of the catheter into the cavity or passage.

In one embodiment, step (b) detects or measures an electrical signal produced as a result of an electrolysis reaction involving a redox reagent.

In one embodiment, the method further comprises processing the electrical signal, e.g. one produced by the redox reaction, to produce a reading which indicates whether the catheter is in a desired environment, e.g. within the gastrointestinal tract. The desired environment may be the stomach.

Methods and apparatus are also provided which may be used to detect whether a catheter is positioned in a pre-selected environment, e.g. positioned in a subject's body correctly, for example before nutritional support and/or drugs are administered using the catheter. The methods and apparatus described herein can also be used to determine whether a catheter has been inserted correctly before samples e.g. fluid samples, are withdrawn from a preselected environment in a subject's body.

Embodiments of the invention include the application of a constant potential difference between the electrodes of a catheter of the invention, when in use. An electrical signal is generated in response to a location-dependent environment where the redox reagent undergoes a redox reaction (electrolysis), charge transfer takes place, the rate of change of which is the current that flows between the two electrodes. In one embodiment, the redox reagent is in electrical contact with an electrode, and as it undergoes the redox reaction, a change in the resistance of the electrical circuit generated by the electrodes occurs, and thus a change in the charge flowing in the electrodes. The change in current is detected using an information processor external to the subject. One such information processor which is suitable for this purpose is described below.

Thus, in some embodiments, the present invention provides a catheter which, when introduced into the correct pre-selected location of a subject, detects an environment specific to said location and results in an electrical signal which can be detected by the user and processed. Thus, a simple, bedside confirmation of correct positioning of the catheter, with minimal risk of adverse effects to the subject is provided.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

DETAILED DESCRIPTION

As described as above, the present invention provides a catheter which comprises a pair of electrodes and a first end portion having a sensing region comprising at least one redox reagent which is in electrical connection with an electrode and which is capable of undergoing a redox reaction when in a selected bodily environment, wherein the rate of the redox reaction is dependent on the selected bodily environment.

In one embodiment, the redox reagent may undergo a redox reaction, the rate of which is dependent on the environment in which the reagent is located, such that the current flowing between the electrode is dependent on the rate of redox reaction and thus the signal produced can indicate whether the current produced is reaches a standard value. In alternative embodiments, the redox reagent may undergo a redox reaction in more than one environment in the subject's body, however, it will not undergo a redox reaction in more than one adjacent cavity or passage to which the catheter may be inserted. For example, when the correct positioning of the catheter in the stomach is to be determined, it will be possible to do so by detecting a redox reaction which is specific for the stomach but is not found, or alternatively found at a significantly different level, in organs or passageways directly connected to the stomach, such as the intestine. A range of redox reactions may therefore be detected, therefore enabling the invention to be applied to a range of bodily environments, without compromising the specificity of the invention.

The redox reagent undergoes an environment dependent reaction, e.g. at a rate dependent on one or more environmental factors. The redox reagent therefore in use undergoes a redox reaction at a rate dependent on the body cavity in which it is located. Some of the features of embodiments of the invention are described in more detail below:

Catheters

In one aspect of the present invention, there is provided a catheter for insertion into a subject's body, which comprises at a proximal end thereof a sensing region for insertion into the subject's body, wherein the sensing region comprises a redox reagent.

A catheter according to the present invention is any invasive tube, catheter, or catheter-like device, which is suitable for insertion into a subject e.g. a body insertion tube. Included are those devices which may not (always) be referred to as catheters (e.g. because they belong to a sub-class of catheter with its own name), but which may be inserted into a subject, such as feeding tubes, cannulae, endoscopes and delivery devices. Typically, the catheters according to the invention may be suitable for administration of fluids or agents, and thus may be flexible in order to negotiate bodily passages. Catheters vary in size, depending upon their proposed use, and the present invention is applicable to all sizes and types of catheter, ranging from, for example, 0.1 mm to 1 cm or more in diameter. Thus, the catheter may have a diameter of for example 0.2 mm, 0.4 mm, 0.5 mm, 0.75 mm, 1 mm, 2 mm, 3 mm, 4 mm, 5 mm, 10 mm, 15 mm, 20 mm, 25 mm, 30 mm, 35 mm, 40 mm, 45 mm, 50 mm or more, as in the case of a veterinary catheter.

Catheters of the present invention for example include peripherally-inserted central venous catheters (PICCs), coronary catheters, pulmonary artery catheters, epidural catheters, central venous catheters, peripheral vascular catheters etc, as well as alternative catheter devices (e.g., feeding tubes such as nasogastric tubes, esophagostomy tubes, gastric feeding tubes, endotracheal tubes, urethral catheters etc.

Examples of other suitable catheters include artificial lung catheters, ear/nose/throat devices (e.g., ear drainage tubes), renal devices, and dialysis articles (e.g., tubing, membranes, grafts), urinary catheters blood pressure and stent graft catheters, implanted drug infusion tubes, central venous access catheters, vascular access catheters, endoscopic surgical tissue extractors, atherectomy catheters, clot extraction catheters, percutaneous transluminal angioplasty (PTA) catheters, percutaneous transluminal coronary angioplasty (PTCA) catheters, drug infusion catheters, angiographic catheters, hemodialysis catheters, neurovascular balloon catheters, drainage tubes, thoracic cavity suction drainage catheters, stroke therapy catheters, abscess drainage catheters, biliary drainage products, dialysis catheters, central venous access catheters, parental feeding catheters. The catheters as listed above may be microporous. In one embodiment, the catheter can be adapted for use by non-medical persons as well as medical professionals.

In one embodiment, the catheter can be adapted for use by non-medical persons as well as medical professionals.

The present invention allows for determining the position of a catheter in relation to a pre-selected environment in a subject. Such environments may include, although are in no way limited to, any passage or cavity which is suitable for receiving a catheter. These include, but are not limited to, blood vessels such as veins and arteries, passages such as the oesophagus, trachea, rectum, urethra, or ureter, cavities including the lungs, stomach, intestine, bladder, chambers of the heart, joints, areas of the reproductive system e.g. the uterus, and ventricles in the brain. In one embodiment, the catheter is for insertion in any bodily environment from which fluid (e.g. blood, cerebrospinal fluid) can be drained, e.g. pulmonary spaces, large bowel, small bowel, peritoneal cavity and pericardium.

The catheter of the present invention typically comprises two ends, each comprising an aperture interconnected by a passageway such that fluid or agents may be received into or discharged from the catheter both inside and outside of the subject. The aperture may be provided at both ends, across the cross-section of the catheter, or alternatively, an end of the catheter may be closed, and an aperture provided in a circumferential (tubular) wall thereof. One end, herein defined as the distal end, typically remains outside of the body when the catheter is in use. It therefore may be adapted to engage with a container, tube or device, which for example may serve as a source of fluid to be supplied to the catheter as a drain for fluid from the body. For this purpose, the distal end of the catheter may comprise suitable engagement means, for example in the form of a male or female connector which is able to connect with a corresponding female or male connector of a container or tube. The other end of the catheter, the proximal end, can be referred to herein as the "insertion end" or "first end region". The proximal end may also be adapted to engage, for example, via its aperture, to a container or device, such as one to be inserted into the body. In one embodiment, the engagement of the catheter to a container or device is reversible.

The catheter of the present invention can be for use in for example a human or a non-human animal. In one embodiment, the subject is a human. In one embodiment, the subject is a non-human animal e.g. a mammal. In one embodiment, the subject can be selected from e.g. a dog, a cat, a horse, a cow, a pig, a sheep, elephant etc.

Electrodes

In one embodiment, the catheter comprises a pair of electrodes, one of which corresponds to an anode and the other of which corresponds to a cathode during use. In one embodiment, the redox reagent undergoes a redox reaction at a predetermined rate when (1) it is located in a selected bodily environment and (2) a potential difference is applied between the electrodes. The redox reaction can be detected, or its rate measured, by monitoring the change in current flowing between the electrodes. Thus, for example, a current may be compared to a reference value to determine whether the redox reagent (the sensing region) is in the desired location. Reference values may be determined empirically.

It will be understood therefore that the term "measuring" as used herein includes comparing an observed value, e.g. current flow through the circuit, with a reference value or standard.

The electrode(s), which are also referred to herein as "electrical conductors", can be formed from any material which is capable of conducting electricity. The electrodes are typically formed from a non-toxic chemically inert and biocompatible material. Suitable electrode materials include those which are capable of transferring electrons as a result of a redox reaction, including for example carbon (e.g. graphite, nanotubes) or an inert metal e.g. gold, platinum, silver, in for example wire, ink or paint format. In one embodiment, the electrodes can be applied to the outer surface of the catheter or a tubular member of the catheter. In any catheter, the electrodes may be the same as each other or different.

In embodiments, the electrodes are preferably attached to the catheter or a tubular member thereof sufficiently securely to prevent or minimize detachment during use, which may be harmful to the subject. This attachment is not necessarily permanent, and the electrodes may be releasable from the catheter in some embodiments. Attachment of the electrodes to the catheter may be achieved by any suitable means, such as wires via a seal, or via printing or painting the electrodes directly onto the catheter.

The electrodes may be longitudinally arranged. In one embodiment, the electrodes are equally spaced on the outer surface of the catheter or a tubular member thereof. In one embodiment, the catheter may comprise more than two electrodes. It is envisaged that a plurality (i.e., two or more) of pairs of electrical conductors may be used, each pair for example being specific for a different biological agent e.g. redox reagent or reduced or oxidised form thereof. In one embodiment, the catheter comprises six, eight or ten, for example, where detecting more than one agent.

It will be appreciated that if more than one redox reagent is used, the information processor, e.g. the transducer, can also be modified such that different currents may be read on different scales, thus allowing combinatorial sensing of the redox reactions. Alternatively, the potential difference applied to the electrodes may be varied to allowed detection of the signals produced by the redox reactions.

Information Processor

As described above, in one embodiment, the catheter comprises a pair of electrodes. In one embodiment, the redox reagent is in electrical communication with one of the electrodes. In use, the pair of electrodes corresponds to a cathode and an anode.

The redox reagent can be in electrical communication, e.g. via the electrode(s), with an information processor which is adapted to detect electrical signals generated by the redox reaction. In one embodiment, the electrodes have a distal end portion which is adapted to be connected to an information processor for detecting or measuring an electrical signal produced by the redox reaction. The catheter may be connected via connectors to the information processor. The information processor typically also processes the signal produced by the redox reaction. The signal may be the current, whose level is detected or measured.

The information processor may process the signal produced by the redox reaction in any of a multitude of ways. Thus, the information processor may be but is not necessarily a microprocessor. In fact, the information processor may be any item that is activated by, responds to, operates on or measures some characteristic of an electric current. For example, information processor may comprise a light bulb, an alarm, an electro-activated switch or any other such devices or combination of devices that operate on an electrical current.

In one embodiment, the information processor is or comprises a detection device for detecting a characteristic of the current or information communicated by the current. The detection device may be in combination with a processor, e.g. a microprocessor to translate the current or information to another form (a numerical value, a reading on a gauge, a new signal, etc.). In one embodiment, the information processor is an ammeter, in which the characteristic would be the magnitude of the current (which may be expressed, for example in milliamperes). An ammeter or other information processor could comprise a display for displaying the amperage of the current; the ammeter could additionally or alternatively comprise a display for indicating a comparison with a reference value.

The information processor may be, or include, a signal transducer which converts a signal produced by the redox reaction to a different signal. Thus, suitable information processors include any means which are able to translate the electrical signal transmitted by the electrical conductors to a detectable indication, e.g. when the electrical current transmitted by the electrodes reaches, or falls on a selected side of, a predetermined threshold value. The indication may be visual, aural, or sensory, such as a vibration or sound signal. In one embodiment, the indication will be visual, for example in the form of a light or other visual display.

In one embodiment, the information processor is adapted to detect or measure the current which flows between the two electrodes. As a result, the information processor can be used to detect whether the catheter is positioned in the current location, since the current flowing between the electrodes will depend on the rate of the redox reaction and thus on the environment of the redox reagent. The information processor can then be calibrated so that current values above (or below) a pre-specified level are considered to represent the correct location of the catheter, whilst current values below (or above) a certain level are considered to represent the incorrect positioning of the catheter.

In one embodiment, the information processor may be calibrated prior to use to correlate to the position of the catheter in the subject's body. The correlation may result from predetermined empirical data or an algorithm, as is well known in the art. In one embodiment, the information processor is calibrated empirically e.g. as a measurement of pH. In an embodiment, the information processor is calibrated in aqueous acid e.g. hydrochloric acid. Other acids may be used to calibrate the information processor e.g. perchloric acid, sulphuric acid, nitric acid, nitrous acid, phosphoric acid or organic acids e.g. citric acid, acetic acid, lactic acid, etc could be used.

In one embodiment, the information processor comprises or is connected to a power source which is adapted to supply a constant potential difference to the electrodes. In one embodiment, the power source is a d.c. power source. The power source may be for example a battery or a solar cell.

In one embodiment, the catheter is for insertion into the stomach of a subject. The pH of the stomach varies between subjects. For example, the pH of a human infant's stomach is usually greater than pH 4, whilst the pH of a healthy human adult can be in the range of pH 1 to 2. Thus, the information processor is typically calibrated taking into account the subject and the bodily environment into which a catheter of the invention will be inserted. For example, when the environment is blood, the partial pressure of oxygen can be used to calibrate the information processor.

In one embodiment, the subject is an infant and the information processor is calibrated assuming a stomach pH of 4. In one embodiment, if the pH of the infant's stomach is considered to be 4, a current reading of greater than for example than about 60 microamps ($\mu A$) is considered to represent the correct positioning of the catheter. Current readings less than about 60 microamps would be considered as "non-stomach" environments and therefore the catheter to be incorrectly placed. The catheter may then be removed from the subject and re-inserted.

Other methods of calibrating the information processor are known in the art.

Also included in the present invention, is a combination of a catheter of the present invention and an information processor for processing (e.g. detecting or measuring) an electrical signal produced by a redox reaction involving the redox reagent. In one embodiment, the information processor e.g. as described above, is adapted to apply a pre-determined potential difference across the electrodes. In one embodiment, the information processor comprises, or is connected to, a d.c. power source. In an embodiment, the d.c. source is for providing a potential difference across a pair of electrodes, one of which is in electrical contact with the redox reagent.

The d.c. power source is typically 1.5 V maximum, e.g. a battery, a solar cell, or other type of device capable of enabling the portable provision of a d.c. power source. The d.c. power source supplies a pre-determined potential difference across the electrodes. Typically, a low voltage d.c. source is used, since the application of alternating currents tends to be hazardous for animals. The information processor may then process an output from the degree of electrolysis that occurs. The readout from the catheter can be incorporated into the information processor, which can be in the form of e.g. a digital reading or a moving coil analogue meter. In addition, the processor can also incorporate a light emitting diode or bulb, which may require transistor-based amplification, to verify the integrity of the catheter and information processor circuits. The processor may also comprise a switch to make the circuit to "test" the system prior to insertion (light "on") and once in the stomach (lights "on" coil in "green area", i.e. stomach). The switch mechanism will limit power usage prolonging power source life-time. Thus, the detection of the positioning of the catheter may be continuous, over multiple intervals or event driven.

In one embodiment, a potential difference exists between the electrodes and the signal is the level of a current flowing through the circuit set up by the electrodes in use, said current resulting from occurrence of the redox reaction.

Thus, in one embodiment, the catheter in use provides a circuit, wherein the redox reagent generates a signal when undergoing a redox reaction such that the electrodes are in electrochemical communication with each other, the signal being input to the circuit. In one embodiment, the circuit comprises an information processor and the information processor translates the signal to information indicative of the location of the catheter.

Agents

In one embodiment, the catheter comprises a binding partner. The binding partner may be any substance having a preferential affinity for a biological agent specific to a pre-selected location into which the catheter is to be inserted. The appropriate binding partner for any particular use of catheter will be determined based upon the nature of biological agent to be detected.

In one embodiment, the binding partner is a redox reagent, whether in oxidised or reduced form. In one embodiment, the redox reagent thereof may bind to protons in the selected bodily environment.

As discussed above, in many embodiments, the catheter of the present invention comprises a redox reagent. In one embodiment, the redox reagent undergoes a redox reaction at a predetermined rate (e.g. a rate which attains, exceeds or falls below a specified threshold) only when the sensing region is inserted into the selected location of a subject's body and not when the sensing region is inserted into another location in the subject's body.

In one embodiment, the redox reagent is biocompatible and non-toxic to the subject. The redox reagent may be selected from Vitamin $K_1$, vitamin $K_2$, vitamin $K_3$, anthraquinones and benzoquinones, e.g. a ubiquinone, phenothiazine and derivatives thereof (e.g. methylene blue, methylene green, and N,N,N'-trialkyl-para-phenylenediamines and N,N-dialkyl-1,4-aminobenzenes). Other examples of suitable redox reagents are ferrocenes and derivatives thereof, ferrocyanides and derivatives thereof and molybdenum cyano complexes, transition metal complexes which are capable of undergoing oxidation or reduction at potentials less than +/−1.0 V vs standard calomel electrode and those which result in dioxygen reduction (e.g. cobalt phthalocyanaine dissolved in an oil phase). The redox reagent is selected based on the preselected bodily environment into which the catheter is intended to be inserted.

For example, in one embodiment, the redox reagent undergoes a redox reaction at a specific pH range found in a specified bodily environment. In one embodiment, the redox reagent is vitamin $K_1$ which can undergo a redox reaction in acid pH and in the presence of for example an environment which corresponds to the stomach environment. The catheter, when the redox reagent is vitamin $K_1$, can be a feeding tube. In embodiments in which vitamin $K_1$ is the redox reagent, the pre-selected bodily environment can be the stomach and the redox reaction may take place in the presence of a hormone, grehlin. In one embodiment, the redox reagent is co-enzyme Q10 (ubiquinone-10).

The redox reagent can be applied to the catheter via a variety of methods. In one embodiment, the redox reagent is painted onto the catheter. In an alternative embodiment, the redox reagent is cross-linked to the catheter via methods known in the art.

In one embodiment, the redox reaction produces a redox product. The sensing region of the catheter may further comprise a regenerating agent which regenerates the redox reagent from the redox product. Alternatively, the sensing region can comprise a precursor of the regenerating agent. The sensing region may comprise at least one layer of a coating comprising the agent or precursor thereof. In one embodiment, the redox reagent is coated with at least one layer comprising the regenerating agent. Alternatively, the regenerating agent may be co-applied with the redox reagent to the sensing region of the catheter. The regenerating agent may be capable of being degraded in the selected bodily environment.

In one embodiment, the agent catalyses regeneration of the redox reagent in the pre-selected bodily environment and thus, the catheter comprises means for catalysing the redox reaction involving the redox reagent. In this embodiment, the electrical signal produced by the redox reaction may be strengthened through the provision of the regenerating agent.

In one embodiment, the sensing region comprises a plurality of layers comprising the regenerating agent. The layers can be in a stepped arrangement, e.g. with there being a proximal portion (i.e. closest towards the insertion end of the catheter) of each layer which is uncoated by a successive layer and each layer, other than the outermost, has a distal portion coated with the next outer layer. In an alternative embodiment, the sensing region comprises a plurality of such layers, in which a distal portion (i.e. a portion which is nearer to the external portion of the catheter) of each layer is coated by a successive layer and each layer, other than the outermost, has a proximal portion coated with the next outer layer. Each layer comprises or consists of the regenerating agent; any layer may include one or more additional materials (e.g. coating material) as well as the regenerating agent.

The number of layers is not essential to the invention and may depend on the intended location of the catheter. The sensing region may comprise 2, 3, 4, 5, 6, 7, 8, 9, 10 or more layers comprising the regenerating agent. In one embodiment, the sensing region comprises between 1 and 5 such layers. In one embodiment, the most proximal portion of the sensing region has one such layer and the most distal portion of the sensing region has 5 such layers of the agent. All the layers may be the same; in embodiments at least one layer differs from every other layer.

In one embodiment, the sensing region may be e.g. 5 cm in length (by way of example only). In some members of this embodiment, the most proximal one centimeter in the sensing area is coated only one time with gelatine. The next centimeter is coated twice; the third centimeter is coated three times; the fourth centimeter is coated 4 times and the fifth centimeter, from the proximal end, is coated 5 times. The differing number of layers allow for time-dependent sensing, as each layer is in turn degraded, thus exposing further redox reagent which can then undergo a redox reaction, at least if located in the correct environment in the subject's body. In one embodiment, the agent is degraded by a process of acid-digested degradation.

In other embodiments, the sensing region may be for example 0.5 cm, 1 cm, 2 cm, 3 cm, 4 cm, 6 cm, 7 cm, 8 cm or greater in length.

The nature or identity of the regenerating agent used will depend upon the environment into which the catheter is intended to be inserted. In one embodiment, the regenerating agent comprises a biocompatible polymer. Examples of suitable regenerating agents include peptide-based polymers e.g. gelatine, milk protein, grehlin, cellulose and fibrin.

In one embodiment, the regenerating agent comprises gelatine. Suitable as gelatine are all commercially available gelatines which can be used for medical purposes, e.g. soft gelatines and hard gelatines, or gelatine compositions possibly containing other additives suitable for medical purposes such as softeners (for example sorbite), glycerol, alkali salts (sodium salts) of ethyl p-hydroxybenzoate or propyl p-hydroxybenzoate, and water or the like. In one embodiment, soft gelatines or a gelatine composition may used which also contain sorbite, glycerol, the sodium salt of ethyl p-hydroxybenzoate, the sodium salt of propyl p-hydroxybenzoate and water.

In one embodiment, the catheter (sensing or non-sensing region) may further a bioactive agent or drug material, e.g. one selected from the group consisting of protein kinase inhibitors, antiproliferative agents, antimitotic agents, antibiotics, antimetabolites, anticoagulants, fibrolytic agents, anti-migratory agents, antisecretory agents, anti-inflammatory agents, non-steroidal agents, angiogenic agents, anti-angiogenic agents, immunosuppressive agents, pyrimidine analogues, purine analogues, spleen tyrosine kinase (SYK) inhibitors and combinations thereof. Generally speaking, a bioactive agent can be coupled to the surface of a catheter or a tubular member thereof by surface modification, embedding or integration and released from within polymeric materials (matrix-type), or surrounded by and released through a carrier (reservoir-type). The polymeric materials in such applications should optimally act as a biologically inert barrier and not induce further inflammation within the body.

In one embodiment, the catheter can also comprise a non-sensing region which comprises electrical insulation. In particular, the electrodes outside the sensing region may be electrically insulated. The non-sensing region or electrodes in this region may be electrically insulated by a coating of an electrically insulating material. In one embodiment, the electrically insulating material is biocompatible and non-toxic. The electrically insulating material may be selected from silicone, Teflon® Tecoflex® (Thermedics), Percuflex™ (Boston Scientific Corporation) and Flexima™ (Boston Scientific Corporation). In one embodiment, the catheter or a tubular member thereof may comprise an electrically insulating layer which may be for example sprayed onto the catheter post-manufacture. In an embodiment, the electrically insulating layer comprises a layer of Teflon®. In an embodiment, the electrodes can be manufactured as an integral part of the catheter. In this embodiment, the catheter may be produced from an electrically insulating material. In a preferred embodiment, the catheter of the invention is insulated to prevent or minimize undesired exposure of the electrical conductors to the subject. In one embodiment, an insulating sleeve is provided over the catheter or a tubular member thereof. The insulating sleeve may be of any non-electrically conductive material, and preferably which is also flexible, water-resistant and/or non-abrasive. Suitable materials include Teflon®.

The catheter may consist essentially of a tube having at one end portion a sensing region and at the opposed end portion connectors for connecting the electrodes to an information processor. The exterior of at least a portion of the tube has electrodes therein and is electrically insulated.

Methods and Uses

In one embodiment, the catheter is for administering of a fluid to an environment in a subject's body. In embodiments, the catheter is for administering drugs to a specified environment or location within the subject's body. Thus, in one embodiment, the catheter can be used to administer a drug to e.g. the subject's stomach, lungs, blood system etc.

In one embodiment, the catheter is a peripherally inserted central venous catheter and can be used to administer drugs to a subject on a continuing basis. The PICC may be implanted into a subject's vein for an extended interval. Drugs can then be either self-administered or are administered by medical personnel. The PICC is typically a soft, flexible tube that can be inserted into a subject's vein surgically.

The catheter of the present invention may be used to administer various drugs to a pre-selected location in the subject's body. Examples of drugs which may be administered using the catheter of the present invention include e.g. parenteral fluids, antibiotics, thrombolytic drugs, steroids, insulin, cytotoxic drugs, etc.

In one embodiment, the catheter is for administering nutritional support to a subject. Thus, the catheter of the present invention can be used to administer an enteral feed to a pre-selected location within the gastrointestinal tract. The enteral feed administered can be a mixture of fat, carbohydrate, protein, water, electrolytes, minerals and fibre, depending on the subject to be fed.

In one embodiment, the catheter is for delivery of a fluid to a selected location in a subject's body. In one embodiment, the catheter is a feeding tube e.g. naso-gastric tube, an esophagostomy tube, and a gastrostomy tube. In one embodiment, the catheter is for the delivery of nutritional support. The catheter, in one embodiment, is for insertion into a subject's stomach so as to deliver nutritional fluids directly to a subject's stomach. This may be particularly useful for subjects who cannot, for whatever reason, derive enough nutrition from their diet alone. This may be for example as a result of illness. In one embodiment, the subject is a human. In an embodiment, the subject is a human infant or child. In one embodiment, the infant can be a premature baby i.e. a baby born before full term of a pregnancy. In one embodiment, the infant is normal term baby which requires feeding via a tube.

In one embodiment, the catheter may be for delivery of fluids to e.g. the blood stream of a subject, to the reproductive system of a subject e.g. an intrauterine tube, to a joint of a subject, e.g. an intraarticular tube. Alternatively, the tube may be for withdrawing fluids from a pre-selected environment. For example, in one embodiment, the catheter can be for the withdrawal of fluids from e.g. a subject's bloodstream, from the spine, or brain, from a joint, from the reproductive system of a subject, from an environment within the gastrointestinal tract of a subject (e.g. from the subject's stomach).

In one embodiment, the catheter of the present invention may be used, once located relative to the correct environment within a subject's body, to collect a sample from the environment. The term "sample" as used herein may include any biological fluid. Examples of samples which may be obtained from biological samples include for example fluids e.g. urine, cerebrospinal fluid, gastrointestinal juices, biliary, pleural, peritoneal, systemic venous, portal venous, arterial, urinary, lymphatic, intracellular or extracellular fluids, and fluids of the male and female reproductive systems, including but not limited to, follicular, menstrual, bulbourethral, amniotic, testicular, seminal and prostatic fluids. Other biological fluids may consist of extracts of cell, tissues and organs of the subject.

The sample may include for example neurotransmitters, hormones, growth factors, cytokines, monokines, lymphokines, nutrients, enzymes, and receptors which are located in the environment in which the sensor is located. The catheter may also be used to withdraw samples which include structured elements e.g. macromolecular structures, organelles and cells, including, but not limited to cells of ectodermal, mesodermal, and endodermal origin such as stem cells, blood cells, neural cells, immune cells, and gastrointestinal cells, and also microorganisms, such as fungi, viruses, bacteria, including but not limited to gram positive and gram negative bacteria, and protozoa.

The samples may be used to indicate the presence of disease e.g. cancer or the presence of infectious pathogens e.g. bacteria, viruses, fungi.

The catheter of the present invention may be used to determine its correct positioning when first inserted into the body. It can also be used to verify its continuing correct positioning, if it is to be located in the subject's body for a length of time. The information processor can be checked by a user to ensure that the read-out indicates the catheter is located correctly. In one embodiment, an alarm is supplied in addition to or as part of the information processor which sounds if the electrical signal produced by the redox reaction changes so that it no longer reaches the threshold value. If the information processor shows that the current no longer reaches the standard value, e.g. by way of an alarm sounding, the user can first check to make sure the information processor is functioning correctly. If so, the user can remove the catheter and reinsert it.

Other Features

Also included in the present invention are methods which comprise the use of a catheter of the invention. In one aspect of the invention, there is provided a method of detecting placement of a catheter comprising a sensing region as described herein relative to a selected environment of a subject's body, comprising;

(a) inserting such a catheter into the subject's body, such that the sensing region becomes inserted into the body;
(b) detecting or measuring an electrical signal produced from a redox reaction.

In one embodiment, the method comprises translating the signal to information indicative of where the catheter is located.

In one embodiment, the method comprises comparing the electrical signal produced with a predetermined value which indicates a threshold value for indicating the correct location of the catheter. In one embodiment in which the catheter comprises a pair of electrodes, the method further comprises applying a potential difference across the electrodes prior to detection of the electrical signal. In one embodiment, the electrical signal is a change in current flowing between the electrodes.

In one embodiment, the electrical signal produced by the method is lower than the threshold value. A value lower than the threshold value may represent incorrect positioning of the catheter. In one embodiment, the electrical signal is the same or higher than the threshold value, potentially representing correct positioning of the catheter. In one embodiment, the method is for determining whether a catheter is positioned in the correct environment in an infant's body. In one embodiment, the method is for determining the positioning of a catheter in a human adult's body.

In a further aspect of the invention, there is provided a method of catheterizing a subject comprising (i) introducing an insertion end of a catheter into a pre-selected location of the subject, the catheter as defined herein, wherein the redox reagent undergoes a redox reaction such that the current flowing between a pair of electrodes changes, (2) detecting said change in current flow which indicates correct positioning of the catheter, and (3) re-positioning the catheter if no change is detected or the change is below a pre-determined level.

The present invention also provides a catheter for insertion into a subject's body, comprising a pair of electrodes, wherein the electrodes are applied to the outer surface of the catheter. Also included in the present disclosure is a catheter having an external end which, in use, remains outside the subject being catheterised and an insertion end for introduction into a pre-selected location in a subject, and a pair of electrical conductors extending therebetween which in use have a constant potential difference between them, wherein at least one of said electrical conductors is in electrical contact with a binding partner for a biological agent specific to said pre-selected location, such that in use binding of a biological agent to said binding partner changes a current flowing in said electrical conductors.

In one embodiment, the binding partner is preferably labelled with an electroactive species which is capable of undergoing a redox reaction to release or take up electrons upon binding of a biological agent thereto. In an embodiment, the electroactive species is selected from electroactive fluorophores including Fluorescein, electroactive proteins such as horseradish peroxidase, and oxoreductases and proteins having Fe—S clusters and those protein having a heme prosthetic group which functions as the redox centre of the protein such as horseradish peroxidase. In one embodiment, the binding partner is any substance having a preferential affinity for a biological agent specific to a pre-selected location into which the catheter is to be inserted. For example, in one embodiment, the binding partner is a monoclonal or polyclonal antibody, antigen, protein including an enzyme or other binding protein, aptamer, oligonucleotide, sugar, and/or a fragment thereof. In one embodiment, the biological agent is any detectable moiety, including an antigen, antibody, oligonucleotide, hormone, aptamer, sugar, protein, or a fragment thereof or a proton. In one embodiment, the binding between the biological agent and the binding partner is specific.

In one embodiment, the binding partner is a redox reagent or a reduced form thereof or an oxidised form thereof and the biological agent is a proton located in a subject's body. In one embodiment, the biological agent is oleoylethanolamide or grehlin.

In one embodiment, two or more binding partners are provided, each specific for a different biological agent and in electrical contact with an electrical conductor on the catheter. In an embodiment, the binding agent is specific for two or more biological agents.

In one embodiment, one or both ends of the catheter comprise means for releasable engagement with a container or device. In an embodiment, the electrical conductors terminate at or immediately proximal to the insertion end. The electrical conductors may extend towards the external end such that they terminate external to a subject. In one embodiment, the electrical conductors are operably connected to signal detection means which upon receipt of an electrical signal from the electrical conductors, provide an indication to the user. In one embodiment, an indication is generated only when a predetermined level of change in the electrical current of the electrical conductor is reached. In one embodiment, the indication is quantitative, dependent upon the amount of biological agent present in any pre-selected location in a subject.

As indicated above, in order for the position of the catheter to be accurately determined, it is preferable to detect a biological agent which is specific for the pre-selected location, or at least a biological agent which will enable a distinction to be made between similar or spatially close cavities or passages. Thus, for example, a suitable biological agent to be detected may be present in various parts of the body, but will not be present in more than one adjacent cavity or passage to which the catheter may be sent. Thus, for example, when positioning of the catheter in the stomach is to be determined, it will be possible to do so by detecting a biological agent which is specific for the stomach—but is not found in organs or passageways directly connected to the stomach, such as the intestine. This effectively broadens the range of biological agents which may be detected, without compromising the specificity of the invention.

Also included in the present invention is a kit of parts comprising (i) a catheter having an external end which, in use, remains outside the subject being catheterised, and an insertion end which is introduced into pre-selected location of the subject, and a pair of electrical conductors extending therebetween which in use have a constant potential difference between them, and (ii) a binding partner for a biological agent specific to the pre-selected location.

In one embodiment, the kit further comprises signal detection means and means for connecting to a d.c. power source.

Also included in the present invention is a method of catheterizing a subject comprising (1) introducing an insertion end of a catheter into a pre-selected location of the subject, the catheter comprising a pair of electrical conductors extending between the insertion end and an external end of the catheter, which in use remains outside the subject, and at least one of the electrical conductors being in electrical contact with a binding partner for a biological agent specific to the pre-selected location, such that binding of the biological agent to the binding partner changes a current flowing in the electrical conductor, (2) detecting the change in current flow in the electrical conductor, which indicates correct positioning of the catheter, and (3) re-positioning the catheter if necessary.

BRIEF DESCRIPTION OF THE DRAWINGS

FIG. 1 shows a catheter of a first aspect having an open insertion end.

FIG. 2 shows an alternative catheter according to the invention.

FIG. 3 shows a longitudinal section of an end portion of the catheter according to the invention, having an open insertion end.

FIG. 4 shows a longitudinal cross-section of an end portion of the catheter shown in FIG. 3.

Figures 5A, 5B:
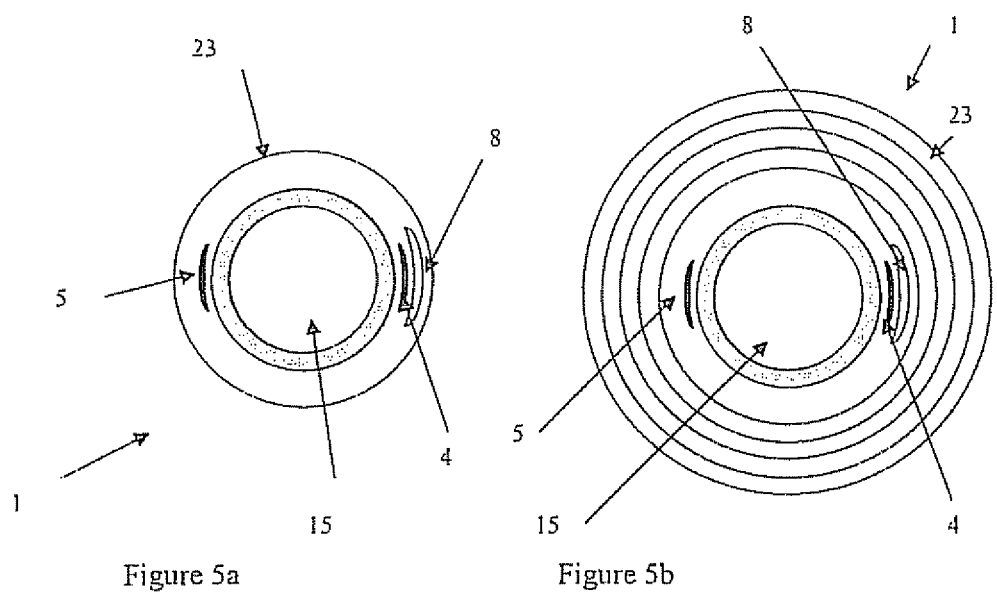
FIG. 5 is a transverse cross-section of a proximal portion of a sensing region as defined herein, with FIG. 5a showing the cross section at a proximal end of the sensing region and FIG. 5b showing a cross section at a distal end of the sensing region.

Embodiments of the invention will be described below with reference to the drawings and the following non-limiting examples.

FIG. 1 shows a cross section of a catheter (1) according to the invention, having an insertion end (2) and a external end (3). A pair of electrodes (4, 5) are provided on the outer surface (6) of the catheter. These extend along a portion of the catheter, and are connected to a display device (not shown) via a connection (7). An insulating layer (8) is provided on the outer surface (9) of the electrodes, extending from the insertion end (2) to the connection of the electrodes (4,5) with the display device, at which point the electrodes leave the outer surface of the catheter (1).

FIG. 2 is a cross section of a catheter (1), in which the insertion end (2) is blind, and an aperture (10) is provided on the longitudinal side (11) of the catheter, proximal to the insertion end (2).

FIGS. 3 to 5 relate to a gastro-nasal tube according to the invention. FIG. 3 is a longitudinal section of an embodiment of catheter (1) according to the invention, having an insertion end (2) and an external end (3). The tube shown in FIG. 3 is a nasogastric tube for use in delivering fluids and food stuffs to a subject's gastrointestinal tract, and is referred to hereinafter as a catheter (1). In other embodiments of the present invention, the catheter is for insertion into other locations and environments within a subject's body.

As shown in FIG. 3, the catheter further comprises an elongate body (13) which defines a lumen (15) which permits movement of fluid to or from a pre-determined location in a subject's body. The elongate body comprises an inlet (not shown) which communicates the tube to a reservoir of fluid. The catheter is typically made from a biocompatible material e.g. a plastic e.g. medical grade PVC, or silicone. Preferably, the biocompatible material is strong enough to avoid collapse of the tube when inserted into a subject's body, but is flexible enough to allow passage of the tube through e.g. a subject's nose.

The subject may be a neonate, infant or an adult. The size of the catheter used in the present invention may depend on the subject and the intended location and use of the tube. For example, a catheter which is for use with an infant will be shorter and have a smaller diameter than a catheter for use in an adult. In one embodiment, the elongate body of the catheter (1) has an outside diameter of approximately 1 mm. Other examples of feeding tubes include e.g. French gauge 3 (1 mm) to French gauge 34 (11.3 mm).

The catheter includes an insertion end (2). The insertion end (2) is for insertion into a pre-selected environment in a subject's body. In the illustrated embodiment, the catheter is for insertion into the stomach of a subject. However, as described herein, the catheter of the present invention can also be suitable for insertion in other locations and environments.

The catheter includes a pair of electrodes. In use, one of the electrodes corresponds to a cathode (4) and one corresponds to an anode (5). The electrodes are provided on an outer surface of the tube. The electrodes (cathode and anode) extend along the length of the elongate body of the tube to the external end (3), and are connected to an information processor, e.g. a display device (not shown) via a connection (not shown). The display device may be part of an information processor which processes the electrical signal produced by a redox reaction involving a redox reagent. In the illustrated embodiment, the electrodes are two separate strips composed of electrically-conductive ink. Each of the electrodes is electrically-insulated from each other on the tube. In other embodiments, the electrodes may be an electrically conductive paint or composite. In one embodiment, the electrodes may be for example conducting wires.

The insertion end is at the proximal most end of a first end region which includes a sensing region (11). At least one of the electrodes or both of the electrodes extend into the first end region. One of the electrodes is in electrical connection with a redox reagent (8). In the illustrated embodiment, the redox reagent (8) is applied to the surface of one of the electrodes. In the illustrated embodiment, the redox reagent is vitamin $K_1$. As shown in FIGS. 3 to 5, the first end region includes an amount of vitamin $K_1$ (8) coated on the cathode (4). Application of the vitamin $K_1$ to the end region is described below but, in short, the one method of applying vitamin $K_1$ comprises sprinkling the catheter with microdroplets of vitamin $K_1$. The vitamin $K_1$ may be applied by dissolving a known amount of vitamin $K_1$ in a volatile solvent (e.g. acetonitrile) to afford a millimolar concentration. An aliquot of this is pipetted over the surface of the tube, and the solvent allowed to evaporate, leaving the vitamin $K_1$ on the cathode. The anode (5) is left unmodified and therefore is not covered by vitamin $K_1$ and therefore Vitamin K is not in electrical connection with the anode.

In one embodiment, the first end region (11), which can also be referred to as a sensing area, (11) is approximately 5 cm long. It will be appreciated that the sensing region may, in some embodiments, be shorter or longer. The sensing region (11) is coated substantially along its length by the redox reagent e.g. vitamin $K_1$, such that the vitamin $K_1$ is in electrical contact with only one of the electrodes, so that electrolysis may be initiated from the base circumference of the vitamin $K_1$ microdroplet that is simultaneously in contact with both electrode and the aqueous environment medium.

The sensing region of the catheter also comprises a regenerating agent as defined herein which is in contact with the redox reagent. The regenerating agent may be capable of enhancing the signal produced by reduction/oxidation of the redox reagent. In one embodiment, the agent is capable of electrocatalysis e.g. as a result of its degradation. The agent can be for example a polymer. In one embodiment, the agent is a protein which is hydrolysed in certain environments, e.g. the pre-selected environment into which the catheter is to be inserted.

In one embodiment, the regenerating agent is gelatine. The sensing region may initially comprise a coating of the agent (23) such that it substantially covers the electrodes (4,5) and the redox reagent (8). Insertion of the sensing region (11) into the pre-selected environment results in the degradation of the regenerating agent, which exposes the layer of vitamin $K_1$.

As shown in FIG. 4 and FIG. 5, the sensing region (11) is differentially coated with differing numbers of layers of gelatine (23). The number of layers may vary between different portions of the sensing region (11). For example, in the illustrated embodiment (see FIG. 4 and FIG. 5), the most proximal one centimeter of the end region is coated with a single layer only. The centimeter of end region next to the most proximal end is coated twice with the gelatine; the third centimeter is coated three times; the fourth centimeter is coated 4 times and the fifth centimeter, from the proximal end, is coated five times. These layers represent different layers for time-dependent sensing based on acid-digested degradation, providing a "location-specific" fingerprint. The agent coating is degraded e.g. by acid digestion.

Thus, at a most proximal end (see FIG. 5a)) of the sensing region, the coating of vitamin $K_1$ and the electrodes may be coated with a single layer of the agent e.g. gelatine (23). Distal from the most proximal region, the sensing region further comprises additional layers of gelatine. Thus, the most proximal end of the sensing region comprises a single layer only of gelatine covering the vitamin $K_1$ microdroplets. The single layer may extend approximately one centimeter along the first end region. The end region may then comprise a portion (19) which includes two layers of gelatine (23) which covers the layer of vitamin $K_1$ applied to the tube underneath. This portion may also extend approximately one centimeter along the length of the first end region of the tube. A third portion (21) of the sensing region includes three layers of gelatine covering the vitamin $K_1$ layer. In the illustrated embodiment, the tube comprises five layers of gelatine, with the most proximal end which extends approximately 1 cm along the tube, having a single layer, the next most proximal portion, of approximately 1 cm in length, including two layers, and so on until the most distal portion of the first end portion having five layers of gelatine.

The staggering of the layers of gelatine allows a "fresh" i.e. previously unexposed layer, of redox reagent to be exposed to the conditions within the pre-determined location e.g. the stomach. As a result, there is a continued supply of redox reagent which undergoes a redox reaction. Thus, the tube of the present invention can be used for a prolonged length of time, if desired, and can be used to detect whether the tube has been dislodged such that it is no longer in the correct environment within the subject's body. Thus, the layer covering the most proximal end will be broken down once inserted into the subject's body thus exposing the most proximal portion of the coating of redox reagent (e.g. vitamin $K_1$). Vitamin K1 undergoes reductive electrolysis into a quinol form (see Wadhawan, et al., Electrochemical studies of vitamin $K_1$ microdroplets: electrocatalytic hydrogen evolution, *Chem Phys Chem,* 2003, 4, 974-82), producing a signal which may be amplified by proteolytic degradation via the gelatine coat and other stomach-specific moieties such as grehlin. The magnitude of the vitamin $K_1$ reduction depends on the specific acidity of the environment (pH≤4 in "normal" humans), giving optimal signals that are enhanced for easy detection.

Once inserted into the correct location, which is detected as discussed above, the tube may be used to deliver fluids to the predetermined location in the subject's body or to withdraw fluids from the predetermined location. The single layer of the gelatine coating is hydrolysed and as a result of the hydrolysis electrocatalyses the redox reaction, thus regenerating vitamin $K_1$ from its reduced form. Hydrolysis of the first layer of gelatine is followed by hydrolysis of the second layer of gelatine, which exposes a previously unexposed portion of vitamin $K_1$. This portion of Vitamin K1 subsequently undergoes a redox reaction, thus providing a continued current flowing between the electrode and thus a signal which indicates that the catheter remains in the correct location. Similarly, the third, fourth and so on layers of protective coating are eventually broken down, thus exposing the vitamin $K_1$ layer underneath.

During use, the tube (1) is connected to an external information processor via two electrical connectors (one to each electrode, not shown) for an external, reusable information processor. Connection can be achieved using adhesive copper tape or other form of simple fabrication that would be known to a person who is skilled in the art.

The tube also comprises an electrically insulating layer (not shown) which is provided on the outer surface of a non sensing region (20) of the catheter. The non-sensing region is distal from the sensing region and can extend the sensing region to the connection of the electrodes (4, 5) with an information processor e.g. a display device, at which point the electrodes leave the outer surface of the catheter (1). The insulating layer may be painted on to the tube and may be for example formed from a material such as Teflon. Other biocompatible materials may be used as an insulating layer.

EXAMPLE 1

Application of Redox Reagent and Regenerating Agent to Cathode

A stock solution of 1 mM vitamin K was prepared. All solutions prepared through pH ranges 0-9 used during experimentation were prepared from 1 M HCl as the starting bulk solution and adjusted accordingly with further HCl for pH<1 and with $Ca(OH)_2/H_2O$ for pH>1. Human gastric juice was adjusted for pH measurements using aqueous $Ca(OH)_2$ or aqueous HCl.

Preparation of Catheters (Conductive Ink, Vitamin K, Gelatin Coating)

Ryle's tubes with both working and reference electrode terminals on a whole catheter, with vitamin $K_1$ and 5 gelatine coats were prepared as follows:

Fast-curing conductive ink (product code 119-03, supplied by Creative Materials, Inc., Tyngsboro, Mass., USA) (2-3 drops on a glass plate) was added to a dish with a thinner (product code 113-12, supplied by Creative Materials, Inc.) (2 drops). The mixture was whisked with a camel hair paint brush until a metallic paint with an even consistency was observed. The paint was evenly applied onto one side of a catheter and allowed to air-dry (for approximately 1-2 hours); the opposite side of the catheter was then also painted in the same way and allowed to air-dry (for approximately 1-2 hours).

Vitamin $K_1$ (20 μL) aliquot was finely layered over the surface of one of the strips on the catheter (working electrode) and allowed to air dry for about 10-15 minutes. The catheter was then dipped with swirling into a sample vial of gelatine/ water (8-12 hours to set) with a depth that totally immersed the whole of the catheter. Studies determined that five coats of gelatine was the optimum coating conditions, hence five separate coats with swirling were applied to the catheter each with a one hour setting/drying period in-between. Coating of the catheter with the desired gelatine coating took approximately three hours.

Finally, copper conductive tape was secured around each of the working and reference terminals, avoiding any contact between the two connections. The catheters were refrigerated to maintain shelf life.

EXAMPLE 2

Several media comprising aqueous HCl at a pH of between 0.5 and ≤6.5, ΔpH=0.2 were prepared. The pH of the medium was adjusted using aqueous HCl or aqueous $Ca(OH)_2$.

The experiment was carried out at room temperature. Three catheters which comprised a region which had been coated with Vitamin K, as described above and with three gelatine coatings were used to determine the current range when −2.0 V is applied between the electrodes. The potential difference was set by a meter employed to operate Clark $pO_2$ electrodes, and was supplied by Hach-Lange, currents measured using an analogue 43-range multitester multimeter, Micronata).

Figure 6:
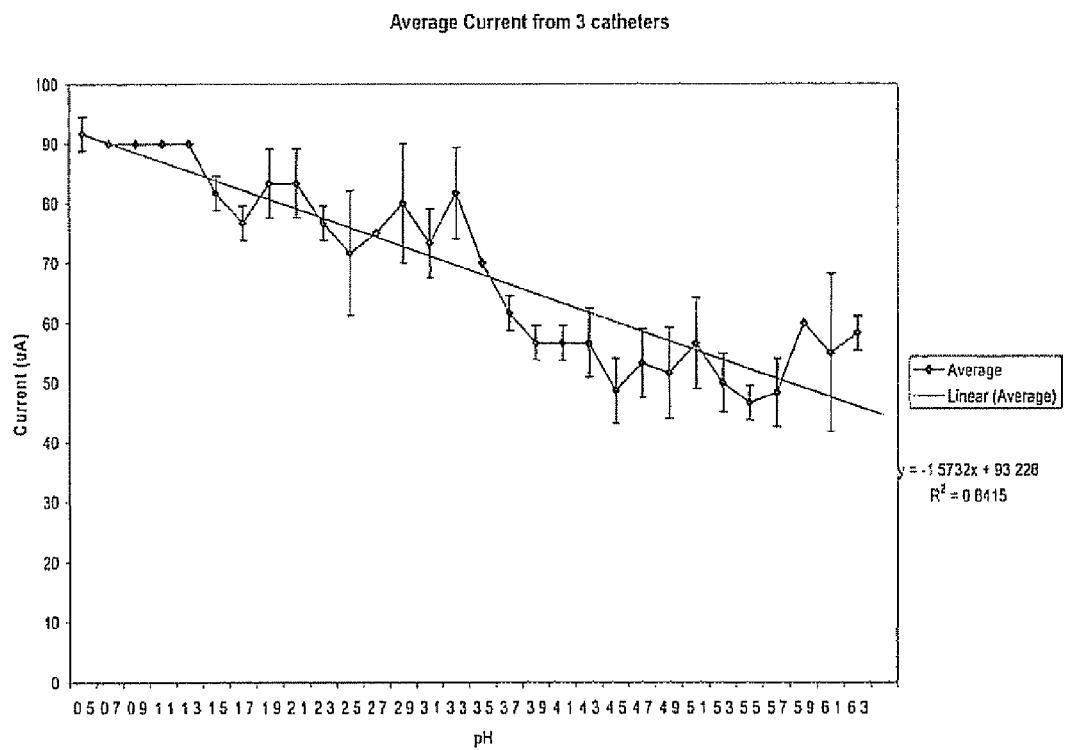
FIG. 6 is a graph showing average current produced from three catheters into media of differing pH.

The results are shown in FIG. 6 which indicates that "stomach" conditions (which typically include a pH of less than 4) are indicated by currents greater than 60 μA.

EXAMPLE 3

Several media were prepared which comprised gastric juice of varying pH, of between 0.5 and 6.5, ΔpH=0.5. The pH was adjusted using aqueous HCl or aqueous $Ca(OH)_2$. The experiments were carried out at room temperature.

Three catheters (with five gelatine coatings) to be used so as to determine the current range when −2.0 V is applied between the electrodes. (Potential difference set by a commercial instrument (Hach-Lange portable Clark $pO_2$ measurement meter, currents measured using an analogue 43-range multitester multimeter, Micronata). The results are shown in FIG. 7.

Figure 7:
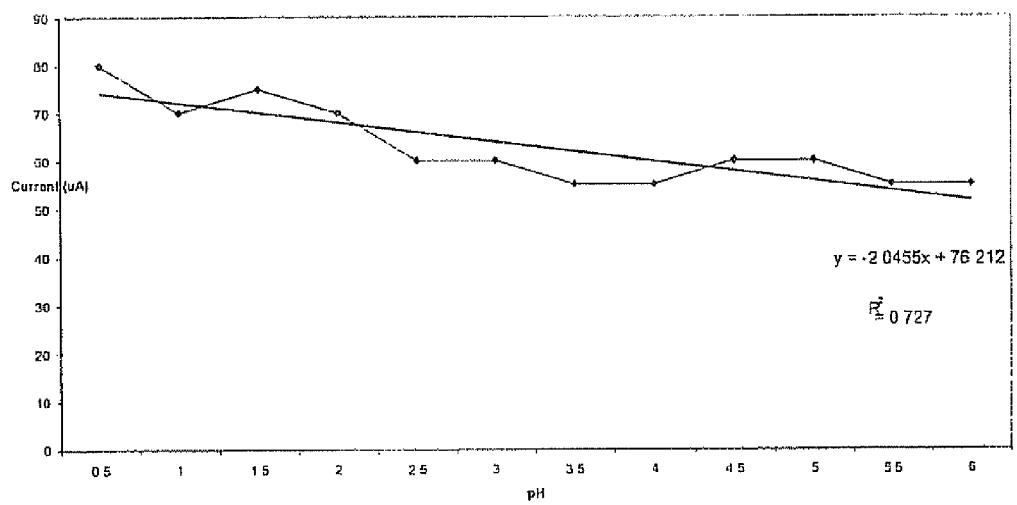
FIG. 7 is a graph showing the average current produced from media containing human stomach juices (obtained from a healthy, young, age 28, male volunteer) with differing pH.

FIG. 7 indicated that there is a defined amperometric cut-off point outside stomach conditions to that observed in the aqueous acid case as above.

EXAMPLE 4

Determining the Effect of Body Temperature on Readout

Various media were prepared which comprised gastric juice of varying pH. The pH varied from 1.0 to 6.0, ΔpH=1.0. The pH was adjusted using aqueous HCl or aqueous $Ca(OH)_2$. The temperature of the media was 37° C.

Two catheters comprising a sensing area with Vitamin K and up to five gelatine coatings were used to determine the current range when −2.0 V is applied between the electrodes. The potential difference was set by a commercial instrument (Hach-Lange portable Clark $pO_2$ measurement meter, currents measured using an analogue 43-range multitester multimeter, Micronata).

Figure 8:
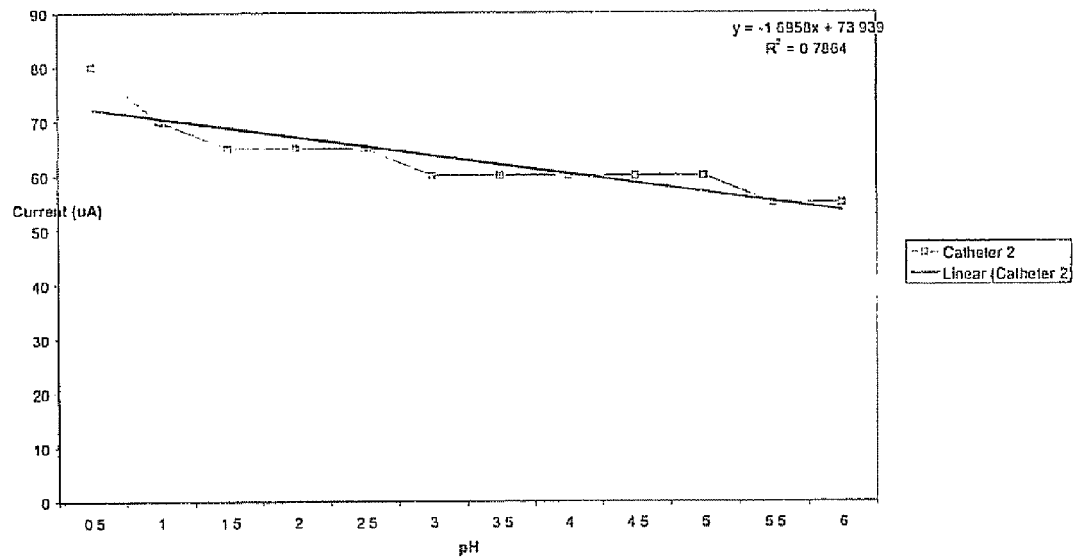
FIG. 8 is a graph showing the average current produced from a media containing human gastric juices (extracted from a healthy, young, age 28, male volunteer) at body temperature.
Figure 9:
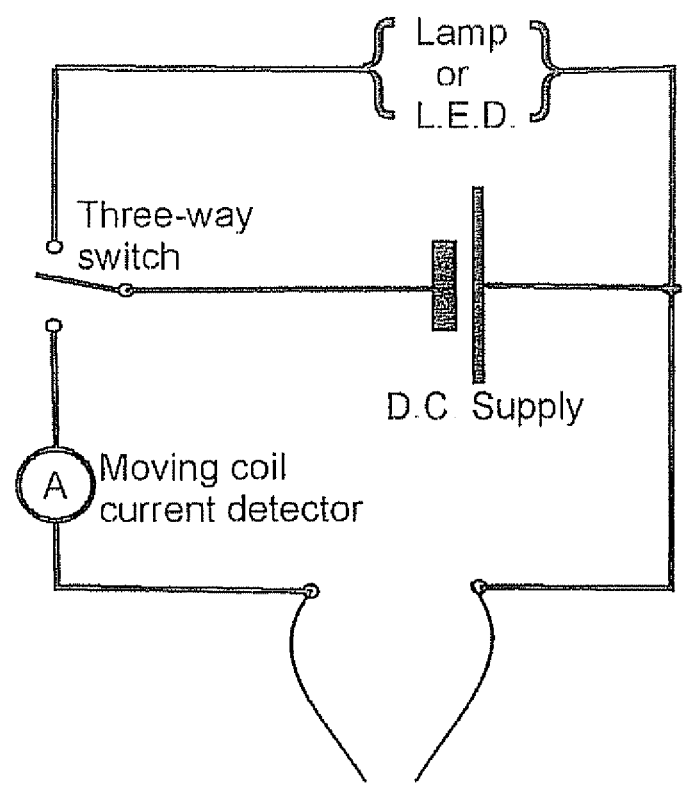
FIG. 9 is an exemplary circuit diagram of the information processor.

As shown in FIG. 8, increasing the temperature to body temperature did not appear to affect the amperometric conditions for determining whether the device is located in the stomach environment or not.

EXAMPLE 5

Use of Other Redox Reagents

The redox reagent ubiquinone-10 was used in a catheter in place of Vitamin K1 and a comparison was made between the two. The medium used was human gastric juice with a pH of 4.0. The temperature of the gastric juice was 37° C.

Two catheters with five gelatine coatings, one coated with vitamin $K_1$ and the other coated with ubiquinone-10, were incubated in the above medium for four days, to quantify (via current measurement) the time-dependence of the catheters. The potential difference was set by a commercial instrument (Hach-Lange portable Clark pO2 measurement meter, currents measured using an analogue 43-range multitester multimeter, Micronata).

The following data were obtained:

|  | Initial current/μA | Current after 4-days of soaking/μA |
|---|---|---|
| Catheter Vitamin $K_1$ | 60 | 2.7 |
| Catheter Ubiquinone-10 | 62.5 | 2.2 |

These data illustrate the degeneration of the gelatine coating over time after thermostatted incubation in the acidic medium. The data show the quinone redox agents (vitamin $K_1$ and ubiquinone-10) function in a similar manner, and undergo electrolysis at approximately the same rate on application of the potential difference between the two electrodes in the circuit.

The invention claimed is:

1. A catheter comprising a first end portion having a sensing region comprising at least one redox reagent which is in electrical connection with an electrode and which is capable of undergoing a redox reaction when in a selected bodily environment, wherein the rate of the redox reaction is dependent on the selected bodily environment, wherein the catheter is a naso-gastric tube and wherein the redox reagent is Vitamin $K_1$ and further wherein the selected bodily environment is the stomach.

2. The catheter according to claim 1, which comprises a pair of electrodes, wherein the redox reagent is in electrical communication with one of said electrodes.

3. The catheter according to claim 1, wherein the redox reagent is in electrical communication with an information processor which is adapted to detect or measure electrical signals generated by the redox reaction.

4. The catheter according to claim 1, wherein the redox reagent is adapted to undergo a redox reaction at a specific rate only when the sensing region is inserted into the selected location of a subject's body and not when the sensing region is inserted into an alternate location in the subject's body.

5. The catheter according to claim 1, wherein the redox reagent undergoes a redox reaction at a specific pH range found in a specified bodily environment.

6. The catheter according to claim 1, wherein the redox reaction produces a redox product, and further wherein the sensing region further comprises a regenerating agent which regenerates the redox reagent from the redox product.

7. The catheter according to claim 6, wherein the sensing region further comprises at least one layer comprising the regenerating agent, wherein said agent is capable of being degraded in the selected bodily environment.

8. The catheter according to claim 7, wherein the sensing region comprises a plurality of layers comprising the regenerating agent, wherein the layers are in a stepped arrangement, there being a proximal portion of each layer which is uncoated by a successive layer and each layer, other than the outermost, has a distal portion coated with the next outer layer.

9. The catheter according to claim 6, wherein the regenerating agent comprises a biocompatible polymer.

10. The catheter according to claim 9, wherein the biocompatible polymer comprises gelatin.

11. The catheter according to claim 10, which further comprises a second end portion at a distal end of the catheter, which is adapted to be connected to an information processor for detecting or measuring an electrical signal produced by the redox reaction.

12. The catheter according to claim 10, wherein the gelatin is capable of regenerating Vitamin $K_1$ from its reduced form.

13. The catheter according to claim 1, which comprises a non-sensing region which is electrically insulated.

14. A combination of a catheter according to claim 2 and an information processor for detecting or measuring an electrical signal produced by a redox reaction involving the redox reagent, wherein in use a potential difference is applied between the electrodes.

15. The combination of claim 14, wherein the information processor comprises, or is connected to, a d.c. power source and further wherein the information processor or the d.c. source, is adapted to supply a pre-determined potential difference across the electrodes.

16. A method of detecting placement of a catheter in a selected environment of a subject's body, comprising:
(a) inserting a catheter according to claim 1 into the subject's body, wherein the sensing region is inserted into the body;
(b) determining an electrical signal produced from a redox reaction, wherein the subject is a neonate, a child or an adult, wherein the sensing region is for placement in the stomach.

17. The method according to claim 16, which comprises applying a potential difference across the electrodes prior to detection of the electrical signal, wherein optionally the electrical signal is a current flowing across the electrodes.

18. The method according to claims 16, further comprising comparing the electrical signal produced with a threshold value.

19. The method for placing a catheter inside a gastro-intestinal tract, comprising:
(a) inserting a proximal end of the catheter within a bodily environment of a subject, wherein the catheter is as claimed in claims 1;
(b) positioning the proximal end of the catheter at a selected location within the gastro-intestinal tract;
(c) detecting an electrical signal produced by a redox reaction involving the redox reagent.

* * * * *